US011195612B2

(12) United States Patent
Orona et al.

(10) Patent No.: US 11,195,612 B2
(45) Date of Patent: *Dec. 7, 2021

(54) APPLICATION LICENSING FOR A CENTRALIZED SYSTEM OF MEDICAL DEVICES (71) Applicant: CareFusion 303, Inc., San Diego, CA (US)

(72) Inventors: Martin Orona, San Diego, CA (US); Aron Weiler, San Diego, CA (US); Patrick Ward, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/593,166

(22) Filed: Oct. 4, 2019

(65) Prior Publication Data
US 2020/0105406 A1    Apr. 2, 2020

Related U.S. Application Data (63) Continuation of application No. 15/419,761, filed on Jan. 30, 2017, now Pat. No. 10,496,792, which is a
(Continued)

(51) Int. Cl.
*G16H 40/20* (2018.01)
*G16H 20/17* (2018.01)
(Continued)

(52) U.S. Cl.
CPC .......... *G16H 40/40* (2018.01); *G06F 21/105* (2013.01); *G16H 20/17* (2018.01); *G16H 40/20* (2018.01);
(Continued)

(58) Field of Classification Search
CPC ............... G06F 21/105; G06F 19/3418; G06F 19/3468; G06F 2221/0768; G06F 21/12;
(Continued)

(56) References Cited

U.S. PATENT DOCUMENTS 4,937,863 A    6/1990 Robert et al.
5,845,065 A    12/1998 Conte et al.
(Continued)

FOREIGN PATENT DOCUMENTS

CN    1701335 A    11/2005
CN    101345670 A    1/2009
EP    0332304 A3    9/1989

OTHER PUBLICATIONS

General-Purpose Infusion Pumps. (2007). Health Devices, 36(10), 309-336.

*Primary Examiner* — Joseph P Hirl
*Assistant Examiner* — Thomas A Gyorfi
(74) *Attorney, Agent, or Firm* — Mintz Levin Cohn Ferris Glovsky and Popeo, P.C.

(57) ABSTRACT

Centralized systems execute one or more applications for monitoring and operating a plurality of network enabled medical devices. An indication to start a selected application at the centralized system or at a network enabled medical device is received at the centralized system/network enabled medical device. The selected application may require a license to operate and, at the time the indication is received, may have a first license available. Instead of using the first license, the centralized system/network enabled medical device may determine to inherit at least a portion of a second license to operate the selected application. The centralized system/network enabled medical device may inherit at least the portion of the second license to form an inherited license, where the inherited license enables features of the selected application. Using the inherited license, the selected appli-
(Continued)

cation is started with the enabled features. Related apparatus, systems, techniques and articles are also described.

20 Claims, 5 Drawing Sheets

Related U.S. Application Data continuation of application No. 13/840,109, filed on Mar. 15, 2013, now Pat. No. 9,558,331.

(51) Int. Cl.
| | |
|---|---|
| *G06F 21/10* | (2013.01) |
| *G16H 40/40* | (2018.01) |
| *G16H 40/63* | (2018.01) |
| *G06F 21/12* | (2013.01) |
| *G16H 40/67* | (2018.01) |

(52) U.S. Cl.
CPC ............ *G16H 40/63* (2018.01); *G16H 40/67* (2018.01); *G06F 21/12* (2013.01); *G06F 21/121* (2013.01); *G06F 2221/0768* (2013.01)

(58) Field of Classification Search
CPC ...... G06F 21/121; G16H 40/20; G16H 20/17; G16H 40/63; G16H 40/40; G16H 40/67
See application file for complete search history.

(56) References Cited

U.S. PATENT DOCUMENTS

| | | |
|---|---|---|
| 6,189,146 B1 | 2/2001 | Misra et al. |
| 6,272,469 B1 | 8/2001 | Koritzinsky et al. |
| 6,584,454 B1 | 6/2003 | Hummel, Jr. et al. |
| 6,810,389 B1 | 10/2004 | Meyer |
| 6,816,842 B1 * | 11/2004 | Singh .................... G06F 21/105 705/59 |
| 6,859,792 B1 | 2/2005 | Marjadi et al. |
| 7,219,222 B1 * | 5/2007 | Durbin ................. G06F 21/305 705/51 |
| 8,230,515 B1 | 7/2012 | Brewton et al. |
| 8,719,949 B1 | 5/2014 | Brewton et al. |
| 8,739,298 B2 | 5/2014 | Biswas et al. |
| 8,789,209 B2 | 7/2014 | Yoakum et al. |
| 8,966,655 B2 | 2/2015 | Womack et al. |
| 2002/0152401 A1 | 10/2002 | Zhang et al. |
| 2003/0135733 A1 | 7/2003 | Hearn et al. |
| 2005/0165693 A1 | 7/2005 | Moritzen |
| 2006/0272004 A1 | 11/2006 | Brockhaus et al. |
| 2008/0005787 A1 | 1/2008 | Aldred |
| 2008/0027871 A1 | 1/2008 | Seo |
| 2008/0140451 A1 | 6/2008 | Hedrick et al. |
| 2009/0113413 A1 | 4/2009 | Reinz |
| 2009/0228976 A1 | 9/2009 | Yamaguchi et al. |
| 2010/0077198 A1 * | 3/2010 | Buck .................... G06F 19/3468 713/100 |
| 2013/0268890 A1 | 10/2013 | Jensen et al. |
| 2014/0230034 A1 | 8/2014 | Le et al. |

* cited by examiner

APPLICATION LICENSING FOR A CENTRALIZED SYSTEM OF MEDICAL DEVICES

CROSS REFERENCE TO RELATED APPLICATIONS

This application is a continuation of U.S. patent application Ser. No. 15/419,761 filed Jan. 30, 2017, which is a continuation of U.S. patent application Ser. No. 13/840,109 filed on Mar. 15, 2013, now U.S. Pat. No. 9,558,331. The disclosures of which are hereby incorporated by reference in their entirety.

TECHNICAL FIELD

The subject matter described herein relates to licensing of applications in a centralized system of medical devices

BACKGROUND

To improve cost efficiency and patient care, hospitals and other care facilities are increasingly using medical devices such as vital signs monitors and infusion pumps. Increasingly, these devices are controlled by electronics including one or more processors. These devices are typically programmable and may be controlled by a centralized system. Both the medical devices and the centralized system often contain multiple applications. A manufacturer of those applications may want to control access to the applications. For example, the manufacturer may limit access to customers that have paid for use of the applications.

SUMMARY

A centralized system executes one or more applications for monitoring and operating a plurality of network enabled medical devices. An indication to start a selected application at the centralized system or at a network enabled medical device may be received at the centralized system/network enabled medical device. The selected application may require a license to operate and, at the time the indication is received, may have a first license available. Instead of using the first license, the centralized system/network enabled medical device may determine to inherit at least a portion of a second license to operate the selected application. The centralized system/network enabled medical device may inherit at least the portion of the second license to form an inherited license, where the inherited license enables features of the selected application. Using the inherited license, the selected application is started with the enabled features.

In some implementations, the selected application may be a command and status application for an infusion pump and/or the selected application may include executable instructions for the centralized system/network enabled medical device. A medical device may be an infusion pump, a vital signs monitor, a ventilator, or other network enabled medical device.

Determining to inherit at least a portion of a second license may include one or more of the following: selecting to use the portion of the second license rather than the first license, determining that the first license is not available or the first license is not valid, reading the portion of the second license from the centralized system and extracting license information applicable to the selected application and determining that the portion of the second license permits use of the selected application.

In some implementations, an indication to start an application that requires a decrypted license to operate at a centralized system may be received at the centralized system. The centralized system may execute applications for monitoring and operating a plurality of network enabled medical devices. Upon decrypting the license to produce a decrypted license, the centralized system may determine that communication with a license server is required. The centralized system may poll the license server with data characterizing the decrypted license to receive a new license, and update the decrypted license based on the new license. In some implementations one or more of the following features may be included: the application may be a command and status application for an infusion pump, the application may include executable instructions for the centralized system, the decrypting may include decryption with an advanced encryption standard, the plurality of network enabled medical devices may include one or more of infusion pumps, vital signs monitors, and ventilators The determining from the decrypted license that communication with a license server is required may include: searching the decrypted license for a limit value to a configuration parameter of the centralized system; searching a configuration of the centralized system for an actual value of the configuration parameter; and determining from the limit value and the actual value whether communication with the license server must be initiated, and/or determining from logic included in the decrypted license that communication with the license server is required.

Computer program products are also described that comprise non-transitory computer-readable media storing instructions, which when executed by one or more data processors of one or more computing systems, causes at least one data processor to perform operations herein. Similarly, computer systems are also described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including but not limited to a connection over a network (e.g. the Internet, a wide area network, a local area network, a wireless network, a wired network, or the like), via a direct connection between one or more of the multiple computing systems, etc.

The current subject matter provides many advantages. For example, the current subject matter enables licensing of applications and features of applications made available at medical devices and centralized systems of medical devices which in turn provides better coordination between application manufacturers and care providers within a healthcare computing environment.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

Like reference symbols in the various drawings indicate like elements.

DETAILED DESCRIPTION

Figure 1:
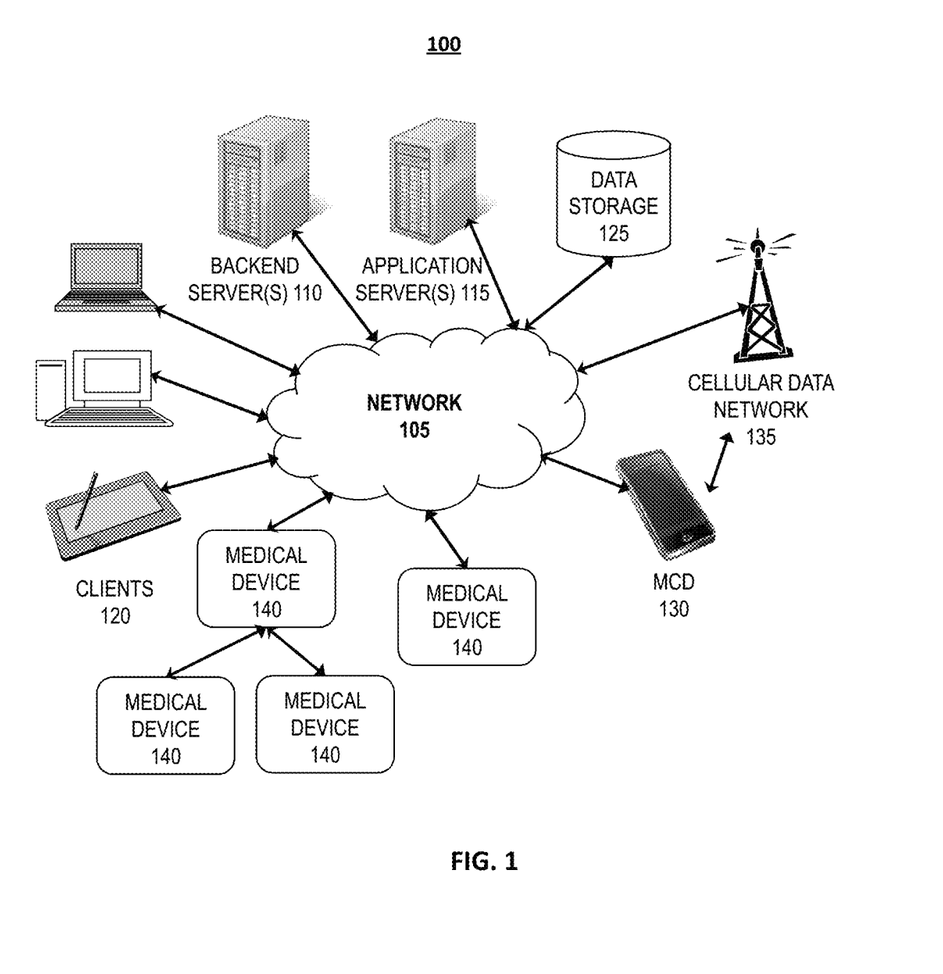
FIG. 1 is a system diagram illustrating a computing landscape within a healthcare environment.

FIG. 1 is a system diagram illustrating a computing landscape 100 within a healthcare environment such as a hospital. Various devices and systems, both local to the healthcare environment and remote from the healthcare environment, can interact via at least one computing network 105. This computing network 105 can provide any form or medium of digital communication connectivity (e.g., wired connection, optical connection, wireless connection, and so forth) amongst the various devices and systems. Examples of communication networks include a local area network ("LAN"), a wide area network ("WAN"), and the Internet. In some cases, one or more of the various devices and systems can interact directly via peer-to-peer coupling (for example, via a hardwired connection or via a wireless protocol such as Bluetooth or WiFi). In addition, in some variations, one or more of the devices and systems communicate via a cellular data network.

In particular, aspects of the computing landscape 100 can be implemented in a computing system that includes a back-end component (e.g., as a data server 110), or that includes a middleware component (e.g., an application server 115), or that includes a front-end component (e.g., a client computer 120 having a graphical user interface or a Web browser through which a user may interact with an implementation of the subject matter described herein), or any combination of such back-end, middleware, or front-end components. A client 120 and server 110, 115 are generally remote from each other and typically interact through the communications network 105. The relationship of the clients 120 and servers 110, 115 arises by virtue of computer programs running on the respective computers and may have a client-server relationship to each other. Clients 120 can be any of a variety of computing platforms that include local applications for providing various functionality within the healthcare environment. Example clients 120 include, but are not limited to, desktop computers, laptop computers, tablets, and other computing devices that may have touch-screen interfaces. The local applications can be self-contained in that they do not require network connectivity and/or they can interact with one or more of the servers 110, 115 (e.g., via a web browser).

A variety of applications can be executed on the various devices and systems within the computing landscape such as electronic health record applications, medical device monitoring, operation, and maintenance applications, scheduling applications, billing applications, and the like.

The network 105 can be coupled to one or more data storage systems 125. The data storage systems 125 can include databases providing physical data storage within the healthcare environment or within a dedicated facility. In addition, or in the alternative, the data storage systems 125 can include cloud-based systems providing remote storage of data in, for example, a multi-tenant computing environment. The data storage systems 125 can also comprise non-transitory computer readable media.

Mobile communications devices (MCDs) 130 can also form part of the computing landscape 100. The MCDs 130 can communicate directly via the network 105 and/or they can communicate with the network 105 via an intermediate network such as a cellular data network or other wired or wireless network. Various types of communication protocols can be used by the MCDs 130 including, for example, messaging protocols such as SMS and MMS.

Various types of medical devices 140 can be used as part of the computing landscape 100. These medical devices 140 can comprise, unless otherwise specified, any type of device or system with a communications interface that characterizes one or more physiological measurements of a patient and/or that characterizes treatment of a patient. In some cases, the medical devices 140 communicate via peer to peer wired or wireless communications with another medical device 140 (as opposed to communicating with the network 105). For example, a medical device 140 can comprise a bedside vital signs monitor with wired and wireless networking capability connected to other medical devices 140, namely a wireless pulse oximeter and to a wired blood pressure monitor. One or more operational parameters of the medical devices 140 can be locally controlled by a clinician, controlled via the network 105 by a clinician, and/or medical devices 140 can be controlled via network 105 by one or more of a server 115, client 120, data storage systems 125, MCD 130, and/or another medical device 140.

The computing landscape 100 can provide various types of functionality as may be required within a healthcare environment such as a hospital. For example, a pharmacy can initiate a prescription via one of the client computers 120. This prescription can be stored in the data storage systems 125 and/or pushed out to other clients 120, an MCD 130, and/or one or more of the medical devices 140. In addition, the medical devices 140 can provide data characterizing one or more physiological measurements of a patient and/or treatment of a patient (e.g., medical device 140 can be an infusion management system, etc.). The data generated by the medical devices 140 can be communicated to other medical devices 140, the servers 110, 115, the clients 120, the MCDs 130, and/or stored in the data storage systems 125.

Medical devices 140 can include any combination of devices such as infusion pumps (e.g., peristaltic pumps, large volume infusion pumps, syringe pumps, patient-controlled analgesia systems, etc.), ventilators, vital signs monitors, and other network enabled medical devices. Commercially available products include ALARIS SYSTEMS MANAGER, ALARIS MEDLEY INFUSION PUMP, and ALARIS INFUSION VIEWER FOR PHARMACY LOGISTICS or similar products from Care Fusion Corporation, San Diego Calif. Many of these products share data and customize a view of the data based on the intended user. Medical devices may both provide patient care and display pertinent information.

In some implementations consistent with FIG. 1, the computing landscape 100 includes a centralized system, medical devices 140, network 105, and cellular network 135. The centralized system includes one or more of clients 120, backend server(s) 110, application server(s) 115, data storage systems 125, and MCD 130. Computing devices 110, 115, 120, 125, and 130 may connect to the network 105 through any wired or wireless access network including cellular data network 135 or other network. Some medical devices 140 can connect directly to network 105, and some medical devices 140 can connect to other medical devices in order to access network 105.

Figure 2:
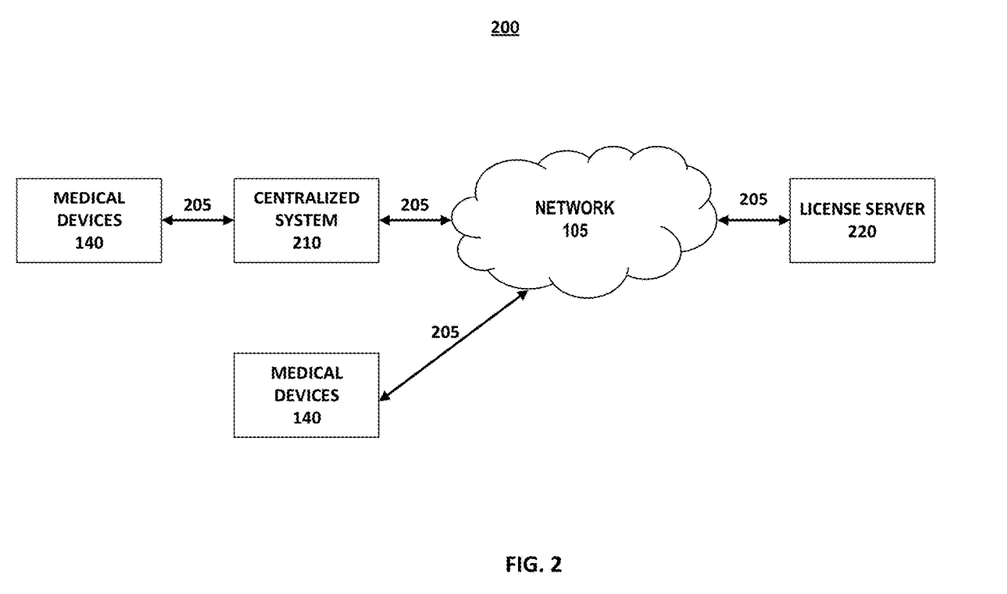
FIG. 2 is a system diagram illustrating a centralized system and medical devices connected through a network to a license server.

FIG. 2 is a system diagram 200 illustrating a centralized system of medical devices connected through a network to a license server. Medical devices 140 can be connected through connections 205 either directly to centralized system 210, through network 105 to centralized system 210, or through another medical device to centralized system 210. License server 220 is also connected to centralized system 210 and medical devices 140 through connections 205 and network 105. License server 220 can provide application licensing information to applications being executed on centralized system 210 and/or medical devices 140. The licensing information can determine what applications are made available and the features made available from those applications at centralized system 210 and medical devices 140.

A centralized system such as centralized system 210 may reside on one or more desktop computing devices and/or portable computing devices. Desktop computing devices include desktop computers with one or more processors, servers, collections of computing devices, distributed computing devices and the like. Portable computing devices include laptop computers, notebook computers, netbook computers, tablet computers, personal digital assistants (PDAs), smartphones, and others such as custom designed computing devices.

Network 105 provides for communication through connections 205 between computing devices such as centralized system 210 and license server 220, and communication through connections 205 between medical devices 140 and centralized system 210. Centralized system 210 can also have a connection to the internet. A user at a user interface, can access the centralized system through a network connection 205. Each connection 205 can be a wired or wireless connection, a serial connection, parallel connection or any other type of communication connection. Connections 205 can also include gateways or routers to provide access through the internet.

A centralized system such as centralized system 210 can connect to between one and thousands of medical devices. In the example of FIG. 2, centralized system 210 connects to medical devices 140 and license server 220 through network 105. Medical devices 140 can connect to centralized system 210 through a switch or router not shown in FIG. 2. The connections 205 between medical devices 140 and the centralized system 210 can be wired or wireless connections, or any combination of wired and wireless connections.

Centralized system 210 can provide commands to medical devices 140. The commands can be individually addressed to one of the connected medical devices, or the commands can be broadcast to multiple medical devices 140. Status data, maintenance data, usage data, and other data can be received at the centralized system 210 from any attached medical device 140. Centralized system 210 can maintain a list of medical devices 140 connected to it. The list of medical devices connected to the centralized system 210 is sometimes referred to as a registry.

Applications that are executable at centralized system 210 can be stored at centralized system 210 and/or data storage 125. An application may be part of a family of applications. A family of applications may include multiple applications related to a particular product. Some applications may be designed to require a license to operate. The license can determine which applications and features are available at centralized system 210. If the license permits use of an application, the license may further determine which features of the application are to be provided. For example, the license may allow use of an application and enable some features of the application but the license may prevent use of other features. In order to make the other features or functions available, the customer/licensee may be required to pay an additional fee, and receive a new license that enables the other features.

The executable files for a complete family of applications can be stored at the centralized system 210 or data storage system 125. A license may permit the use of all the applications in the family of applications, or the license may permit the use of a subset of the family of applications. Without the license, the application cannot be operated. For example, a customer/licensee may have purchased a license for one of the applications in the family of applications. Despite the customer/licensee having a license for just one of the applications, the executable files for the entire family of applications may be stored at the centralized system 210. In addition to the executable files already stored at the centralized system 210, the addition of a license may be all that is needed to operate that application.

If the customer/licensee wishes to enable additional features of existing applications and/or enable applications not previously licensed, the customer/licensee may gain access by paying any associated fees to the manufacturer and receiving a new license. With the new license, the additional features of existing applications and/or new applications are made available.

The license can be stored at centralized system 210 or at data storage 125. When an application is started, the license is read to determine if the license permits operation of the application. The licensed features of the application are determined by the license. In some implementations, the license can be stored at an application server 115 or backend server 110, or may be provided by license server 220 through connections 205, network 105, and the internet each time an application is started.

Applications that are executable at medical devices 140 can be stored at the medical devices 140, or at centralized system 210 and/or data storage 125. Applications executable at the medical devices 140 may require a license to operate. The license can determine which applications are available at medical devices 140. If the license permits use of an application, the license may further determine which features of the application are enabled. For example, the license may allow use of an application and enable some features of the application but the license may prevent use of other features. In order to make the other features available, the customer/licensee may be required to pay an additional fee, and receive a new license that enables the other features.

The license for an application available at a particular medical device can be stored at that medical device. When an application is started, the license is read and the available features of the available applications are determined based on the license. In some implementations, the license can be stored at centralized system 210, data storage 125, or may be provided by license server 220 through connections 205, network 105, and the internet, each time an application is started.

A license can be a file or a unique text string generated by license server 220. The file may be in the form of a text file, binary file, or other file. For example, the license can be a text file stored at centralized system 210 that enables a particular subset of features of an infusion viewer application executable at the centralized system 210. In another example, the license for an application executable at medical device 140 can be a binary file stored at the medical device 140. The license can contain logic that interacts with centralized system 210 and/or medical devices 140. For example, the license may limit a number of medical devices to 3000 that are permitted to be connected to the centralized system 210. In this example, 2500 medical devices are connected to centralized system 210. The license logic may interact with centralized system 210 and generate a notification that the number of connected medical devices is close to the limit. The notification can be sent to a user of the centralized system and/or to the license server 220 in order to notify the user and/or manufacturer that the license may need to be upgraded to accommodate additional medical devices.

The license can include information about an expiration of the license. For example, the license can contain an expiration date after which the license expires. To determine whether the license has expired, the centralized system 210 can compare the date of the centralized system 210 clock with the expiration date in the license. As the date from the clock approaches the expiration date, a warning may be generated that the license is about to expire. When the clock reaches the expiration date, the centralized system 210 may disable the applications and/or features or functions of the applications related to the license. In some implementations, when the expiration date is a predefined number of days (or less) into the future, the centralized system may generate a notification message indicating the upcoming expiration date. The notification can be sent to a user of the centralized system 210 or to the license server 220.

The license can contain information about the customer/licensee. For example, information about the company name, address, and approved administrators may be included in the license. In some implementations, this information can be used by the centralized system 210 and license server 220 to verify the authenticity of the license, and to assist in verifying that the license has not been unscrupulously duplicated by someone that does not own the license The license can be encrypted so that the license can only be read by a device with the proper encryption/decryption algorithm and encryption/decryption parameters. For example, once the encryption/decryption parameter has been provided to the centralized system 210, the centralized system 210 is able to decrypt the license from license server 220. From the decrypted license, the centralized system 210 determines which applications and features of the applications are permitted to be used by the customer/licensee. Encryption/decryption of the license may include encryption/decryption techniques such as Advanced Encryption Standard (AES) or other techniques. Stated differently, in the context of the enabled features of an application or device being changed by a license, the encryption/decryption technique described herein can be implemented in a manner in which only the systems and devices that the license was intended for, will the license change or enable the functionality. In the event that a license is corrupted, invalid, or irrelevant for a specific application or device, the encryption/decryption technique will ensure that no changes to the functionality will be implemented and the operator applying the license will be notified through the communication paths shown in FIG. 2.

The license may be generated by license server 220. The license server 220 may be located at a manufacturer's facility. Centralized system 210 may have access to the license server through connections 205 and network 105. Network 105 may include a connection through the internet and/or one or more routers not shown in FIG. 2. For example, a customer/licensee may purchase a license for an application. The manufacturer can generate the license for the customer/licensee. The license may be sent to the customer/licensee from the license server 220, through connections 205, network 105 and the internet, to the customer's/licensee's centralized system 210. The license is then utilized as described above. Alternatively, the license generated by license server 220 may be sent to centralized system 210 as an attachment to an email, a short message service message, or other means for delivering the license to centralized system 210.

A user interface (e.g., a graphical user interface, etc.) to access a centralized system can facilitate sending commands and receiving information from a device connected to the centralized system 210. Before sending commands or accessing information, authentication of the user at the user interface may be required. The user may be required to provide authentication information at the user interface and may be required to provide additional authentication information to the centralized system 210. Upon successful authentication, the user can send commands to centralized system 210 and/or to medical devices 140 connected to the centralized system and/or receive information form the medical devices 140 and/or centralized system 210.

The authentication credentials of a user can limit the types of commands that a user is permitted to send, the types of information the user is permitted to receive, and/or or the medical devices that the user may access. For example, a particular user may be permitted to receive only maintenance information from the medical devices 140 on centralized system 210 and no other information, and may not be permitted to send commands to medical devices 140. In this example, a user limited to maintenance data may be appropriate for maintenance personnel at a hospital. Other examples include the physician for a patient who may be authorized to adjust a dosage level at a medical device where maintenance personnel would not be authorized to adjust dosages. Other limitations or sets of limitations are also possible.

Although the foregoing descriptions and processes were explained in the context of applications and licenses at a centralized system 210, the descriptions and process also apply to medical devices 140.

Figure 3:
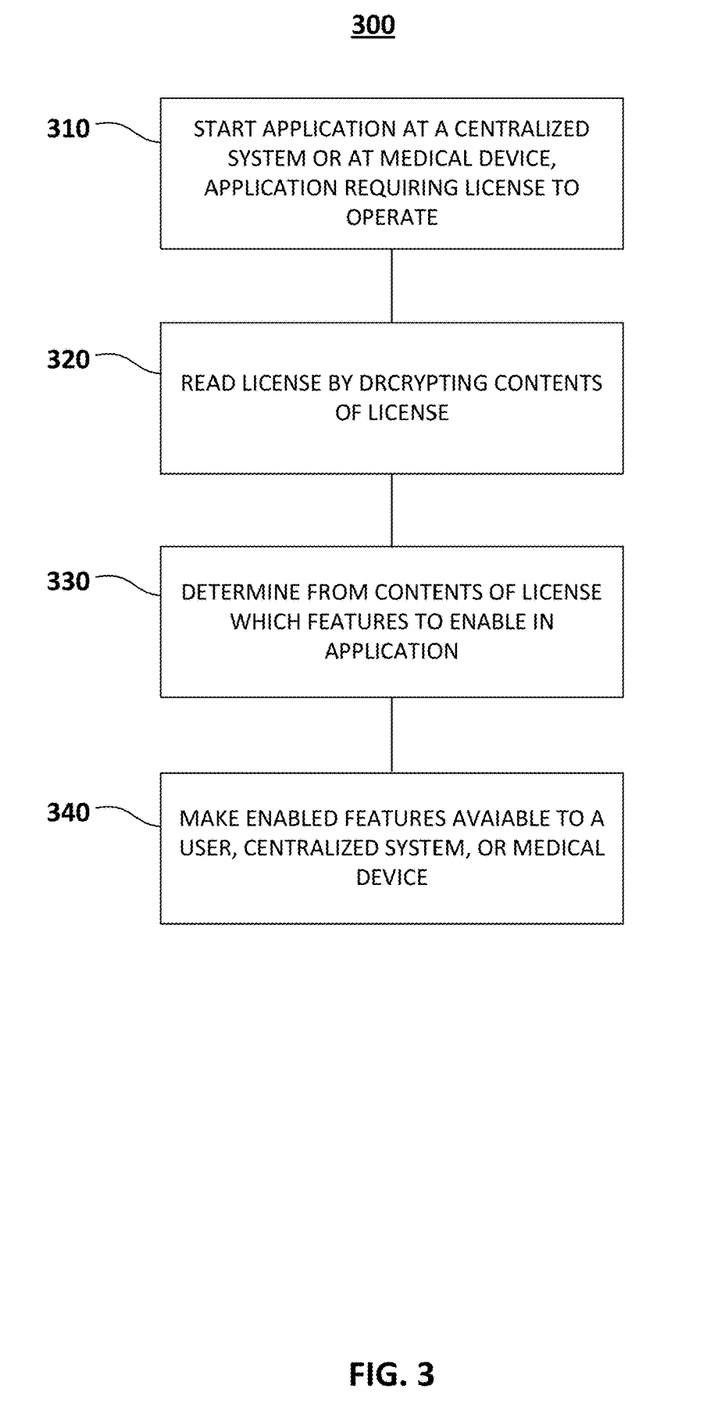
FIG. 3 is a process diagram illustrating enabling features of an application using a license.

FIG. 3 is a process diagram 300 illustrating a license that determines whether an application is made available, and if it is made available, the features of the application that are made available. At 310 an application requiring a license to operate is started at centralized system 210. At 320, the license is read by decrypting the contents of the license at the device where the application will operate. At 330, the contents of the license determine if use of the application is permitted, and if permitted, the features of the application that are permitted. At 340, when the license permits use of the application, the application and the features enabled by the license are made available to a user, centralized system, or medical device.

At 310 an application requiring a license to operate is started at centralized system 210. For example, an application for monitoring and controlling infusion pumps (e.g. infusion viewer) may be started at centralized system 210. As part of starting the application, configuration information from the centralized system 210 may be read. For example, the configuration information may include number of medical devices connected to the centralized system 210.

At 320, the license is read by decrypting the contents of the license at the device where the application will operate. For example, if the license server 220 that generated the license used the advanced encryption standard (AES) with a predetermined set of encryption parameters, then the license may be decrypted using AES decryption and the same encryption parameters to reveal the contents of the license. The contents of the license can determine the applications and features available at the device. The AES algorithm as used herein may be based on permutations and substitutions. Permutations are rearrangements of data, and substitutions replace a unit of data with another. AES may perform permutations and substitutions using different techniques. AES encryption and decryption algorithms may use a key schedule generated from a seed key array of bytes. An implementation that generates multiple keys from an initial key instead of a single key greatly increases security. Other encryption techniques are also possible.

At 330, the contents of the license determine if use of the application is permitted, and if permitted, the features of the application that are permitted. The contents of a license may permit use of one application or multiple applications. For each permitted application, the license may permit use of one or more features of the application. For example, the license may permit two applications with one feature of the first application being permitted and three features of the second application being permitted.

The license may also contain logic that includes configuration information from centralized system 210 or computing landscape 100 to determine if the customer/licensee is close to exceeding a licensed feature. For example, the contents of the license may reveal that an application is licensed for use with a limited number of medical devices. For example, the maximum number of medical devices 140 connected to centralized system 210 may be limited to 3000. In this example, the number of medical devices connected to centralized system may be determined to be 2999 from the configuration information at centralized system 210. The logic in the license may determine that the number of devices connected to the centralized system 210 is within the permitted maximum and thus permit use of the application. The logic may cause the generation of a notification that the number of medical devices is close to the permitted maximum. The notification may be sent to a user of the centralized system 210 and/or may be sent to the license server 220. The notification sent to the license server 220 can be used by the manufacturer to sell an upgraded license to ensure that the license permits a sufficient number of medical devices to meet the customer's/licensee's needs.

At 340, if the license permits use of the application, the application and the features enabled by the license are made available to a user, centralized system 210, or medical device 140. Continuing the above example, with 2999 medical devices connected to centralized system 210, the license determines that the application is permitted to operate. In some implementations or applications, if the number of medical devices 140 connected to centralized system were not 2999 but instead 3100, the application may be disabled or a feature of the application may be disabled because the number of connected medical devices exceeds the maximum. In other implementations or applications, exceeding a licensed feature may not cause an application or feature to be disabled but instead may result in additional notifications or other responses.

The license features such as the above-noted number of medical devices that are permitted to be connected to centralized system 210 do not necessarily constitute hard limits. In some implementations, the application and its features may not be disabled but instead more frequent notifications may be sent to the user. For example, notifications may be generated at various intervals such as every time the application is started, or every day, or every ten minutes. The notifications may require a response by a user of centralized system 210 such that the inconvenience of the notifications and responses provides sufficient motivation to the customer to purchase an appropriate license. A notification may also be sent to the manufacturer through connections 205, network 105, and the internet to license server 220. The notifications can allow the manufacturer to collect license fees for the actual usage of the customer/licensee.

Although foregoing description of a process by which a license that determines whether an application is made available at a centralized system 210, and if it is made available, the features of the application that are made available, the process also applies to licenses and applications at a medical devices 140.

Figure 4:
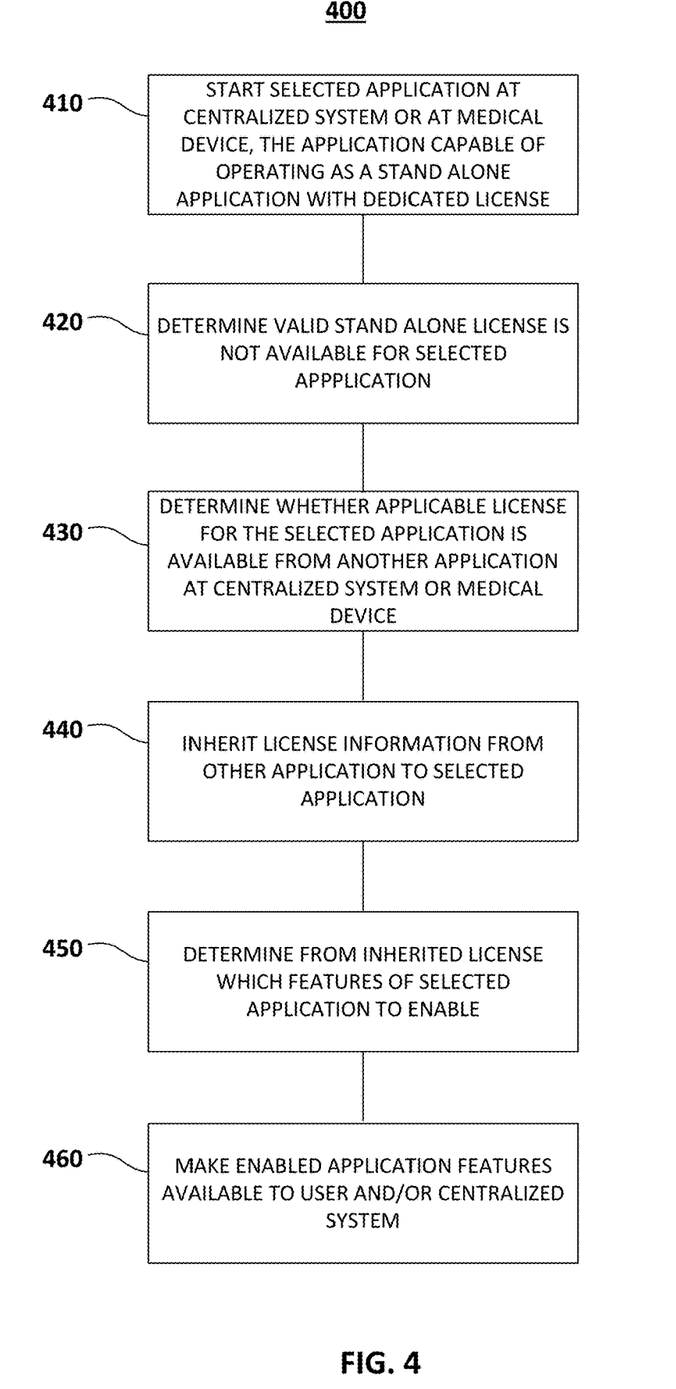
FIG. 4 is a process diagram illustrating inheriting a license at a selected application from another license at another application.

FIG. 4 is a process diagram illustrating inheriting a license at a selected application from another license for another application. At 410, a selected application requiring a license to operate is started at a centralized system 210. The selected application is capable of being operated with a stand-alone license, if available. At 420, the centralized system 210 determines that a stand-alone license is not available for the selected application. At 430, the centralized system 210 determines whether an applicable license for the selected application is available from another license at the centralized system 210. At 440, an applicable license is inherited at the selected application from the other license. At 450, the centralized system 210 determines from the inherited license which features of the selected application to enable. At 460, the centralized system 210 makes available to the user, centralized system 210, and/or medical device 140 the enabled features of the selected application.

At 410, a selected application requiring a license to operate is started at a centralized system 210. The selected application is capable of being operated with a stand-alone license, if available. A stand-alone license is a license to operate just the selected application. For example, a customer/licensee may purchase a stand-alone license for monitoring and controlling infusion pumps such as an infusion viewer application. The stand-alone license allows the customer/licensee to operate just the infusion viewer application. The stand-alone license that permits use of the infusion viewer application does not itself permit use of other applications. In contrast, a license that is not stand-alone may license the use of multiple applications. Some applications can be licensed with either a stand-alone license or a license that is not stand-alone. In some implementations, the application may be one of a closely related family of executable programs. For example, a family of applications may correspond to applications associated with a particular product line such as a particular infusion pump product line.

At 420, the centralized system 210 determines that a stand-alone license is not available for the selected application. For example, an infusion viewer application may be started on the centralized system 210. The infusion viewer application requires a license to operate. Upon start-up, the infusion viewer application may search for a stand-alone license. The result of the search may be that no stand-alone license is found for the infusion viewer application, or the result may be that a stand-alone license is found but is not valid, or the result may be that a stand-alone license is found but a user or application has selected that a stand-alone license not be used. Examples of reasons why a stand-alone license may be invalid include the license may have an expiration date that has passed, or the stand-alone license may be valid for one family of medical devices (e.g. one infusion pump product family) but a different family of medical devices is connected to the centralized system 210.

At 430, the centralized system determines whether an applicable license for the selected application is available from another license for another application at the centralized system 210. The centralized system may search for licenses under which the selected application can be operated. When one application can use a license or a portion of a license associated with another application, the license is said to be inherited. For example, upon the start of an infusion viewer application, and with no stand-alone license found, the centralized system may search for a license for another application whose license includes a license for the infusion viewer application. In this example, the license for the other application also includes a license for the infusion viewer application and may include licenses for additional applications as well. In some cases, more than one applicable license for the selected application may be found at the centralized system. When more than one applicable license could be used, logic at the centralized system or a user will select which license to use to operate the selected application. Different licenses may have different application features enabled. For example, one license may allow 2500 medical devices to be connected to an infusion viewer application, and another applicable license may allow 5000 medical devices. Depending on the license selected by the logic at the centralized system or selected by the user, the number of permitted medical devices connected to the centralized system may have different values. This may affect the number of allowable devices before a notification is generated that the system is close to the maximum allowable by the selected license.

At 440, an applicable license is inherited at the selected application from the other application. If more than one applicable license is available, the user or centralized system 210 selects which of the applicable licenses to inherit in order to operate the selected application.

At 450, the centralized system determines from the inherited license which features of the selected application to enable. The inherited license can enable features of the selected application. Logic may be included in the inherited license that interacts with configuration information from centralized system 210 and/or medical devices 140. For example, if the number of medical devices 140 is close to the maximum, a notification may be generated as described above.

At 460, the centralized system 210 makes available to the user or centralized system the enabled features of the selected application. Based on the inherited license, the selected application provides the enabled features subject to any logic contained in the inherited license.

Although the foregoing description of license inheritance is directed toward a selected application at a centralized system 210 inheriting an applicable license from another application at a centralized system 210, the applicable license can also be inherited from an application at medical device 140 to centralized system 210, or from an application at one medical device 140 to an application on another medical device 140, or from an application on a medical device 140 to an application at a centralized system 210.

Figure 5:
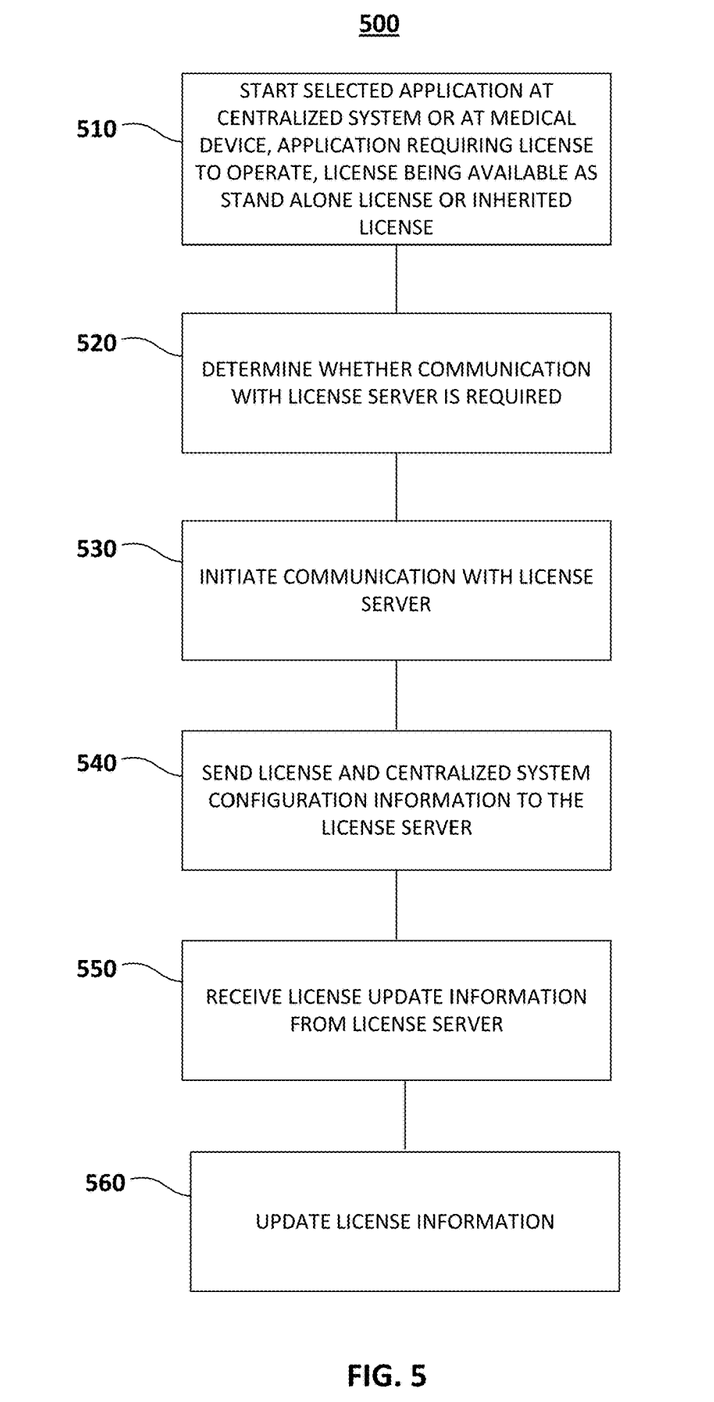
FIG. 5 is a process diagram illustrating a license server updating a license.

FIG. 5 is a process diagram illustrating a license server 220 updating a license. At 510, a selected application requiring a license to operate is started at a centralized system 210, the license being available as a stand-alone license, or as an inherited license. At 520, the centralized system 210 determines whether communication with a license server 220 is required. At 530, the centralized system 210 initiates communication with the license server 220. At 540, license information is sent from the centralized system 210 to the license server 220. At 550, the centralized system 210 receives license update information from the license server 220. At 560, the license at the centralized system 210 is updated.

At 510, a selected application requiring a license to operate is started at a centralized system 210. A license may be available as a stand-alone license or as an inherited license. If no license is available, in some implementations the selected application may still be started but without the features that require a license to be enabled. In other implementations, starting the application may result in little or none of the functionality that the selected application provides with a license. In this case, starting the application may result in simply checking for a license.

At 520, the centralized system determines whether communication with a license server 220 is required. An indication that communication with a license server 220 is required may be determined from the license, or the indication may be determined from the selected application, or the indication may be determined from logic in the license that interacts with the selected application. For example, the selected application may be an infusion viewer application. Upon starting the application, an inherited license may be selected. In this example the inherited license permits a maximum of 3000 medical devices 140 connected to the centralized system 210, and the centralized system 210 has 2550 medical devices connected to it. In this example, logic in the license may determine that when the maximum is reached with fewer than 500 additional medical devices 140, the license server 220 may be contacted to alert the manufacturer that the infusion viewer license is close to the maximum number of permitted medical devices 140. This benefits the customer/licensee by ensuring that the license meets the needs of the customer/licensee and it benefits the manufacturer by providing information that can be used to ensure that the manufacturer is paid for the license that meets the customer's/licensee's needs. Another example of a feature of the license that may require communication with the license server is an expiration date of the license that is within a predetermined number of days of the current date. Other features may also require communication between the centralized system 210 and license server 220.

At 530, the centralized system 210 initiates communication with the license server. In some implementations, the license server 220 is connected through connections 205 and through network 105 to centralized system 210 and medical devices 140. In some implementations, the communication through network 105 may include communication through the Internet. The license server 220 may provide a web portal, short message service interface, or other means to communicate with centralized system 210 and/or medical devices 140. For example, centralized system 210 may communicate with license server 220 through a web portal where information can be exchanged including license information. Initiating communication may include establishing a secure connection between the license server 220 and the centralized system 210 and/or medical devices 140. The secure connection may include a transport layer security (TLS) connection, secure sockets security (SSL) connection, or other secure connection.

At 540, the license information is sent from the centralized system 210 to the license server 220. Once communication has been initiated and any required security established between the license server 220 and the centralized system 210, the centralized system 210 can pass the license information related to the selected application to the license server. Configuration information from the centralized system 210 can also be sent. Continuing the previous example, with the selected application being an infusion viewer application, the license information passed to the license server 220 includes information such as the maximum number of medical devices permitted by the license. For example, the configuration information passed from the centralized system 210 to license server 220 may include the number of medical devices connected to the centralized system 210. Other information related to the license may also be sent with the license to the license server 220. Also, other configuration information of the centralized system 210 including the type, and/or status of the medical devices 140 connected to the centralized system 210 may be sent.

The license server 220 may also receive information related to the license form the manufacturer. For example, the customer/licensee may have purchased an updated stand-alone license or updated license from which the selected application has inherited the license. For example, the customer/licensee may have purchased an upgraded license permitting 5000 medical devices to be connected to the centralized system instead of 3000 medical devices. The manufacturer may provide an updated license to license server 220 reflecting the upgraded license.

At 550, the centralized system 210 receives license update information from the license server 220. Continuing the above example, the license server 220 can send an updated license to the centralized system 210 through the network 105. For example, the updated license may allow 5000 medical devices instead of 3000. The updated license may also include newly enabled features of the selected application. The updated license may also enable additional applications that were not previously licensed to the customer/licensee.

At 560, the license at the centralized system is updated. In some implementations, the updated license is stored at the centralized system 210. In other implementations, the license can be stored at data storage 125. When the selected application is started, a determination is made whether communication with the license server 220 is needed. If the centralized system 210 determines that the license server 220 does not need to be contacted, the centralized system 210 may operate the selected application according to the license and without communication with the license server 220. In some implementations, when the centralized system 210 determines that the license server must be contacted and the license server is unavailable due to a connection problem through the network or internet, or other problem, the selected application may continue to operate according to the previous license until communication with the license server is successful. In other implementations, if the license server 220 cannot be contacted, the selected application may be disabled until communication with license server 220 is successful.

In other implementations, the license may not be stored at the centralized system 210 or data storage 125. When the selected application is started, the centralized system 210 must communicate width he license server 220 and the license must be sent from the license server before the application can be operated.

Although the foregoing description of the use of a license server 220 is directed toward a centralized system 210 communicating with a license server 220, a medical device 140 can also communicate with a license server 220 in the same manner.

One or more aspects or features of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device (e.g., mouse, touch screen, etc.), and at least one output device.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flow(s) depicted in the accompanying figures and/or described herein do not necessarily require the particular order shown, or sequential order, to achieve desirable results. Other implementations may be within the scope of the following claims.

What is claimed is:

1. A medical device system comprising:
   a processor; and
   a memory, wherein the processor and the memory are configured to perform operations comprising:
   receiving, from a licensing server, a first license for a first medical device application and a second license for a second medical device application, wherein the first license and the second license are assigned to a site;
   receiving, from a first medical device associated with the site via a network for the site, a request to start a selected application at the first medical device, wherein the selected application requires a license to operate;
   identifying, after receiving the request, a portion of the first license includes an applicable license to operate at least one feature of the selected application;
   transmitting, to the first medical device via the network, the portion of the first license to form an inherited license, wherein the inherited license causes the first medical device to enable the at least one feature of the selected application; and
   causing the first medical device to start the selected application with the at least one feature.

2. The medical device system of claim 1, wherein the first license is a license to operate only selected features of the selected application.

3. The medical device system of claim 2, wherein the at least one feature enabled by the inherited license is different from the selected features enabled by the first license.

4. The medical device system of claim 1, wherein the selected application is a command and status application for an infusion pump.

5. The medical device system of claim 1, wherein the processor and the memory are further configured to perform an operation comprising determining that the applicable license to operate at least one feature of the selected application is available from at least a portion of the second license, wherein the second license allows the first application to operate.

6. The medical device system of claim 5, wherein determining comprises selecting to use the at least a portion of the second license rather than the first license.

7. The medical device system of claim 5, wherein determining comprises determining that the first license is not available or the first license is not valid.

8. The medical device system of claim 5, wherein determining comprises:
   reading the portion of the second license from the second medical device and extracting license information applicable to the selected application; and
   determining that the portion of the second license permits use of the at least one feature of the selected application.

9. The medical device system of claim 1, wherein the first medical device comprises one of an infusion pump, a vital signs monitor, and a ventilator.

10. The medical device system of claim 1, wherein the selected application comprises executable instructions for the first medical device.

11. A method, comprising:
    receiving, from a licensing server, a first license for a first medical device application and a second license for a second medical device application, wherein the first license and the second license are assigned to a site;
    receiving, from a first medical device associated with the site via a network for the site, a request to start a selected application at the first medical device, wherein the selected application requires a license to operate;
    identifying, after receiving the request, a portion of the first license includes an applicable license to operate at least one feature of the selected application;
    transmitting, to the first medical device via the network, the portion of the first license to form an inherited license, wherein the inherited license causes the first medical device to enable the at least one feature of the selected application; and
    causing the first medical device to start the selected application with the at least one feature.

12. The method of claim 11, wherein the first license is a license to operate only selected features of the selected application.

13. The method of claim 12, wherein the at least one feature enabled by the inherited license is different from the selected features enabled by the first license.

14. The method of claim 11, wherein the selected application is a command and status application for an infusion pump.

15. The method of claim 11, further comprising determining that the applicable license to operate at least one feature of the selected application is available from at least a portion of the second license, wherein the second license allows the first application to operate.

16. The method of claim 15, wherein determining comprises selecting to use the at least a portion of the second license rather than the first license.

17. The method of claim 15, wherein determining comprises determining that the first license is not available or the first license is not valid.

18. The method of claim 15, wherein determining comprises:
    reading the portion of the second license from the second medical device and extracting license information applicable to the selected application; and
    determining that the portion of the second license permits use of the at least one feature of the selected application.

19. The method of claim 11, wherein the first medical device comprises one of an infusion pump, a vital signs monitor, and a ventilator.

20. The method of claim 11, wherein the selected application comprises executable instructions for the first medical device.

* * * * *